(12) United States Patent
Perler

(10) Patent No.: US 9,468,532 B2
(45) Date of Patent: Oct. 18, 2016

(54) SEMI CONSTRAINED POLYAXIAL ENDOPROSTHETIC ANKLE JOINT REPLACEMENT IMPLANT

(71) Applicant: Adam D. Perler, Carmel, IN (US)

(72) Inventor: Adam D. Perler, Carmel, IN (US)

(*) Notice: Subject to any disclaimer, the term of this patent is extended or adjusted under 35 U.S.C. 154(b) by 0 days.

(21) Appl. No.: 14/453,789

(22) Filed: Aug. 7, 2014

(65) Prior Publication Data

US 2015/0045902 A1 Feb. 12, 2015

Related U.S. Application Data

(60) Provisional application No. 61/863,394, filed on Aug. 7, 2013.

(51) Int. Cl.
*A61F 2/42* (2006.01)
*A61F 2/30* (2006.01)

(52) U.S. Cl.
CPC .... *A61F 2/4202* (2013.01); *A61F 2002/30227* (2013.01); *A61F 2002/30354* (2013.01); *A61F 2002/30604* (2013.01); *A61F 2002/30845* (2013.01); *A61F 2002/30848* (2013.01); *A61F 2002/30884* (2013.01); *A61F 2002/30892* (2013.01); *A61F 2002/4205* (2013.01); *A61F 2002/4207* (2013.01)

(58) Field of Classification Search
CPC ............... A61F 2/4202; A61F 2002/4205; A61F 2002/4207
See application file for complete search history.

(56) References Cited

U.S. PATENT DOCUMENTS 8,668,743 B2 * 3/2014 Perler ............... A61F 2/4202
623/21.18

* cited by examiner

*Primary Examiner* — Brian Dukert
(74) *Attorney, Agent, or Firm* — Bruce J. Bowman

(57) ABSTRACT

A semi-constrained polyaxial ankle joint replacement implant has a dual bearing component, a tibial component or plate adapted for attachment to a tibia or fibula bone, and a talar component or plate adapted for attachment to a talus or calceneus bone of the foot. The dual bearing component includes a superior bearing providing gliding articulation/translation between it and the tibial component, and an inferior bearing providing gliding articulation/translation between it and the talar component. The tibial plate has peripheral transversely extending flanges that semi constrain or limit movement relative to the superior bearing and/or vice versa. The inferior bearing has a flange extending upwardly from the superior surface thereof that is received in an opening in the intermediate plate to semi constrain or limit movement relative between the two components.

13 Claims, 12 Drawing Sheets

SEMI CONSTRAINED POLYAXIAL ENDOPROSTHETIC ANKLE JOINT REPLACEMENT IMPLANT

CROSS REFERENCE TO RELATED APPLICATIONS

This non-provisional patent application claims the benefit of and/or priority under 35 U.S.C. §119 to U.S. Provisional Patent Application Ser. No. 61/863,394 filed Aug. 7, 2013, entitled "Polyaxial Endoprosthetic Ankle Joint Replacement Implant" the entire contents of which is specifically incorporated herein by this reference.

This non-provisional patent application is also related to and specifically incorporates herein by reference U.S. patent application Ser. No. 13/286,760 filed Nov. 1, 2011, entitled "Prosthetic Device with Multi-Axis Dual Bearing Assembly and Methods for Resection."

BACKGROUND OF THE INVENTION

1. Field of the Invention

The present subject matter is directed generally to orthopedic prostheses, joint replacement systems and methods and, more particularly, to a multi-axis mobile bearing ankle prosthesis.

2. Background Information

The concept of total ankle arthroplasty has a long and relatively unsuccessful history due to the high failure rate often associated with the original implant devices and implantation techniques. Only recently has total ankle arthroplasty regained some recognition as a viable treatment for limited indications and as a viable alternative to an ankle joint fusion, which is often referred to as the gold standard of treatment. It has been shown that replacement of an ankle joint with an ankle prosthesis can be particularly challenging due to the relatively small articular contact surfaces of the ankle, complex biomechanics of both the ankle and hindfoot joints, limited and risky access to the ankle joint during replacement, and wide variation in patient candidacy. Past flawed design rationale and the above factors have led to a high rate of post-operative complications such as loosening of the ankle prosthesis, subsidence, pain, abnormal ankle prosthesis wear, and/or meniscal/bearing breakdown—often leading to ankle implantation failure.

In addition to the technical difficulties, regulatory agencies have classified ankle prosthetics in a manner which is often viewed as substantially limiting scientific progress in the field of ankle replacement due to the financial burden of obtaining market clearance for such devices.

Currently, two classes of ankle prosthetics are generally available; a semi-constrained ankle prosthetic and an unconstrained ankle prosthetic. Both types of ankle prosthetics utilize either a three (3) piece and two (2) component design (with the meniscal portion/bearing locking into the tibial plate) or a three (3) piece and three (3) component design (with a mobile/unlocked bearing) including an upper, middle, and lower component (tibial, bearing, and talar component, respectively).

A semi-constrained ankle prosthesis typically provides a tibial fixation component (usually metal) which provides firm attachment to the distal end of the tibia bone. A talar component provides firm attachment to the superior surface of a prepared talus, and provides on its upper or proximal side a surface for articulation. A bearing component can fit between the tibial component and the talar component and is typically locked/fixed to the tibial component. The underside of the bearing can provide a surface to articulate with the surface of the talar component. These surfaces can be structured such that all motions present in a normally aligned ankle joint can be at least partially replicated. Such motions can include plantar/dorsiflexion, rotation about the tibial/talar axis, some medial/lateral translation, and some anterior/posterior translation. Rotations in the frontal plane or motion in the transverse plane are usually not well supported as there is little curvature in this region. The influence of the subtalar joint axis of motion is not generally taken into consideration with this type of the device, which can alter the function and position of the talar body and therefore the talar component. These motions can occur actively and lead to edge loading, causing higher stress and greater propensity for wear. Also, as the articular surfaces can be designed for mismatch, even under optimum implant positioning and loading, higher stress will be seen at the contact point due to the point loading associated with mismatched radii of the articular surfaces as the surface contact areas are smaller and thus experience much greater loads.

Unconstrained prosthetics are all generally the same in function. They are similar to semi-constrained prostheses except that the potential for motion between the tibial component and the bearing component is designed into the prosthesis with anterior to posterior rotation of the ankle in the sagittal plane and gliding motion in the transverse plane. There is not intimate fit between the bearing component and the tibial component as the tibial component usually has a flat undersurface and the bearing component usually has a simple flat upper surface so that translation and rotation are allowed at this interface. Further, the interface between the talar component and the bearing component can have a curvature that is matched, so there is a large contact surface area and optimized contact stress that can result in reduced wear. This matched articulation can be accomplished because other motions are allowed for between the tibial and bearing components. It has been clearly shown with clinical history in all joints that if these motions are not allowed for, the force must be absorbed at the implant bone interface, and can lead to a greater propensity for loosening. The current systems in this category do not often address the frontal plane motion influence of the underlying subtalar joint axis.

Therefore, it is apparent from the above that the need exists for a polyaxial endoprosthetic ankle joint replacement implant.

It is also apparent from the above that the need exists for a better semi constrained polyaxial endoprosthetic ankle joint replacement implant.

SUMMARY OF THE INVENTION

The present invention is a semi constrained polyaxial (endoprosthetic) ankle joint replacement implant. A dual bearing component of the semi constrained ankle joint replacement implant, along with first and second bone anchoring components, provides semi constrained polyaxial and independent movement with respect to both the first and second bone anchoring components.

The present semi constrained ankle joint replacement implant (or prosthesis) includes a dual bearing component, a tibial component or plate adapted for attachment to a tibia or fibula bone, and a talar component or plate adapted for attachment to a talus or calceneus bone of the foot. The dual bearing component includes a superior bearing providing gliding articulation/translation between it and the tibial component, and an inferior bearing providing gliding articulation/translation between it and the talar component.

The dual bearing component includes a bearing component plate that provides a base or foundation for the superior and inferior bearings. The superior bearing is bonded to the bearing component plate while the inferior bearing moves with respect to the bearing component plate.

The talar component has an inferior surface with a bone fixation portion for fixation to a talus or calceneus (in the event of a non-viable talar bone) and a superior surface designed for articulation with the inferior bearing of the dual bearing component. The inferior bearing of the bearing component has an inferior surface for articulation with the superior surface of the talar component through congruent complimentary articulating surfaces. The tibial component has a superior surface with a bone fixation portion for fixation to the tibia bone or a fibula bone, and an inferior surface for articulation with the superior bearing of the bearing component through smooth surfaces of the two.

The polyaxial mobile bearing component has a smooth superior surface adapted for gliding on a smooth inferior surface of the tibial component to allow desired rotational and translational movements. The polyaxial mobile bearing component has a contoured inferior surface that is mostly congruent with a contoured superior surface of the talar component which allows for frontal plane motion, but limits the transverse and sagital plane motion. The inferior surface has a proximal surface that is mostly congruent with a distal aspect of the proximal bearing while the distal aspect of the inferior surface is mostly congruent with the superior surface of the talar component and allows for mostly sagittal plane rotation/motion/excursion.

In accordance with an aspect of the present invention, the tibial plate has peripheral transversely extending flanges that semi constrain or limit movement relative to the superior bearing and/or vice versa. The inferior bearing has a flange extending upwardly from the superior surface thereof that is received in an opening in the intermediate plate to semi constrain or limit movement relative between the two components.

BRIEF DESCRIPTION OF THE DRAWINGS

The above mentioned and other features, advantages and objects of this invention, and the manner of attaining them, will become apparent and the invention itself will be better understood by reference to the following description of the invention taken in conjunction with the accompanying drawings, wherein.

Figure 1:
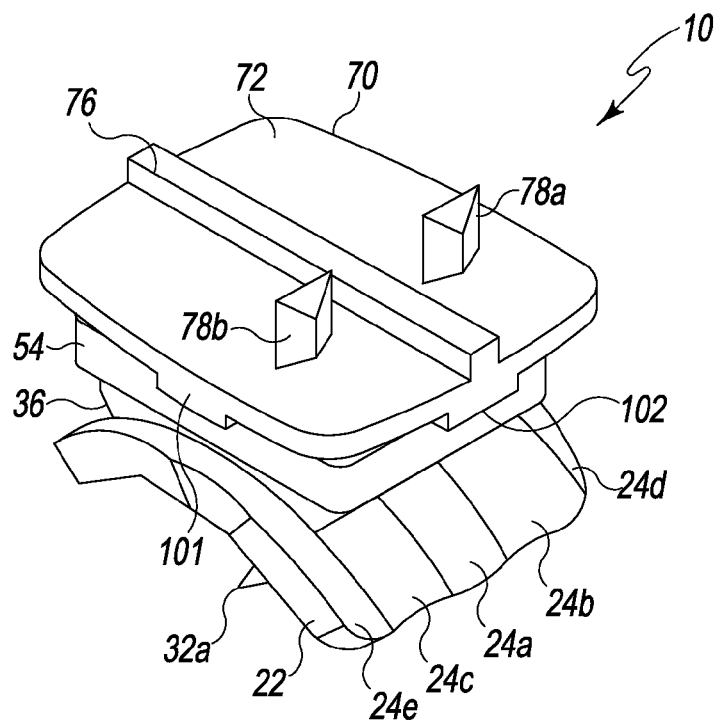
FIG. 1 is an isometric superior/lateral view of a semi constrained right ankle joint replacement implant fashioned in accordance with the principles of the present invention.

Like reference numerals indicate the same or similar parts throughout the several figures. A detailed description of the structures, features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION OF THE INVENTION

Figure 2:
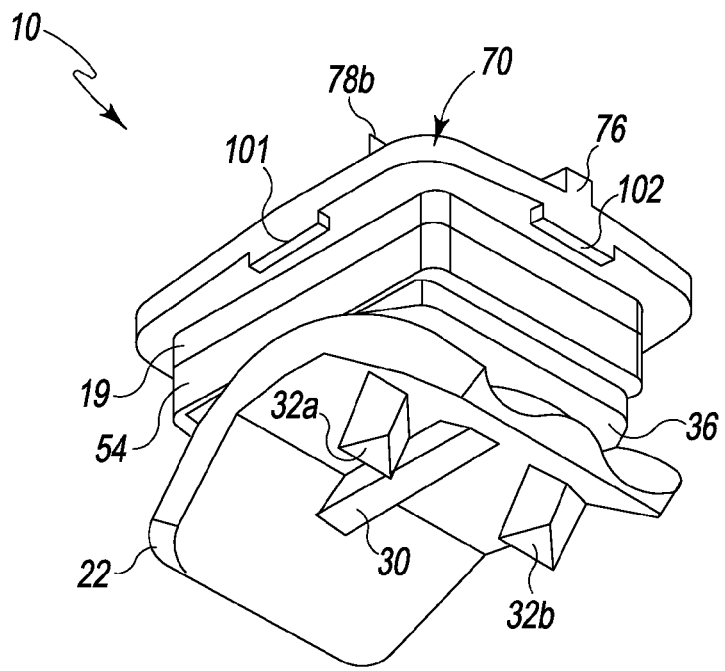
FIG. 2 is an isometric inferior/lateral view of the present semi constrained right ankle joint replacement implant.
Figure 3:
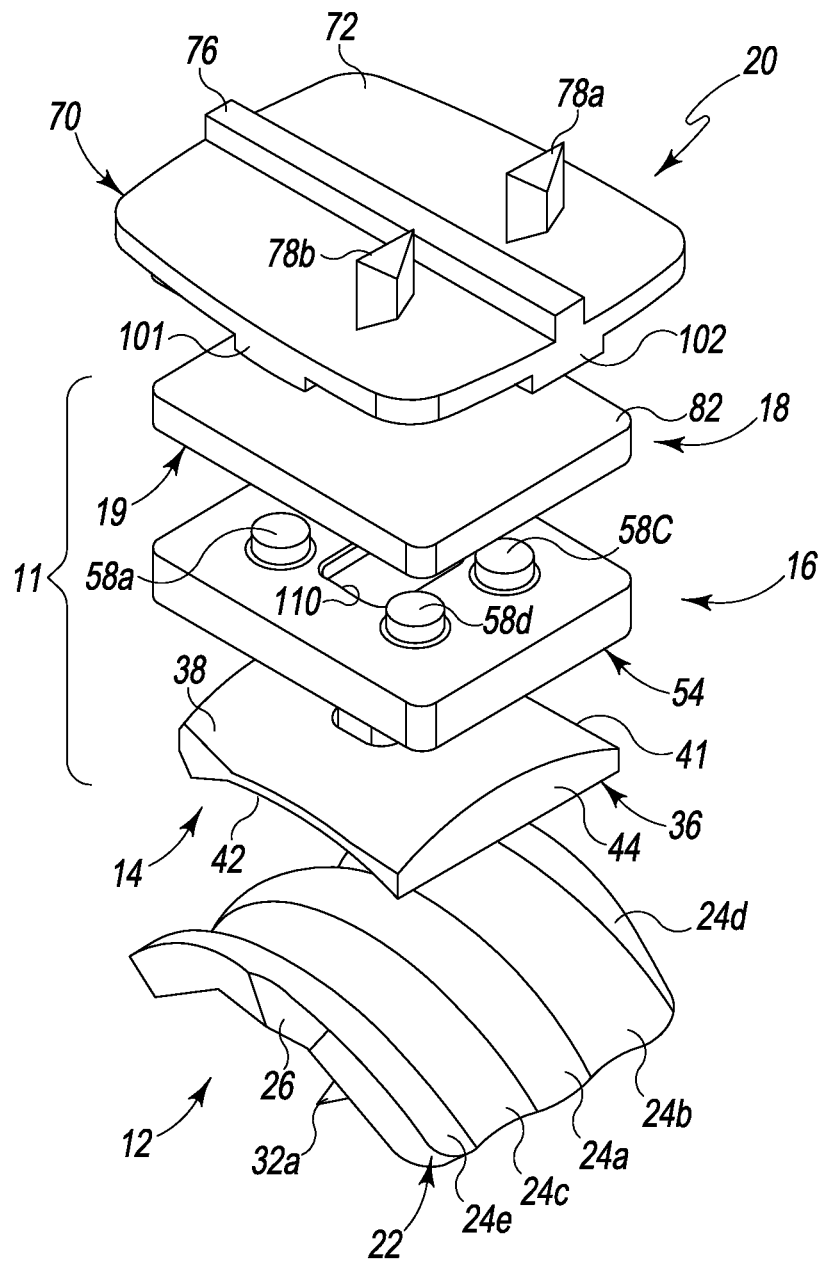
FIG. 3 is an exploded isometric superior view of the present semi constrained right ankle joint replacement implant from an anterior/lateral viewpoint.
Figure 4:
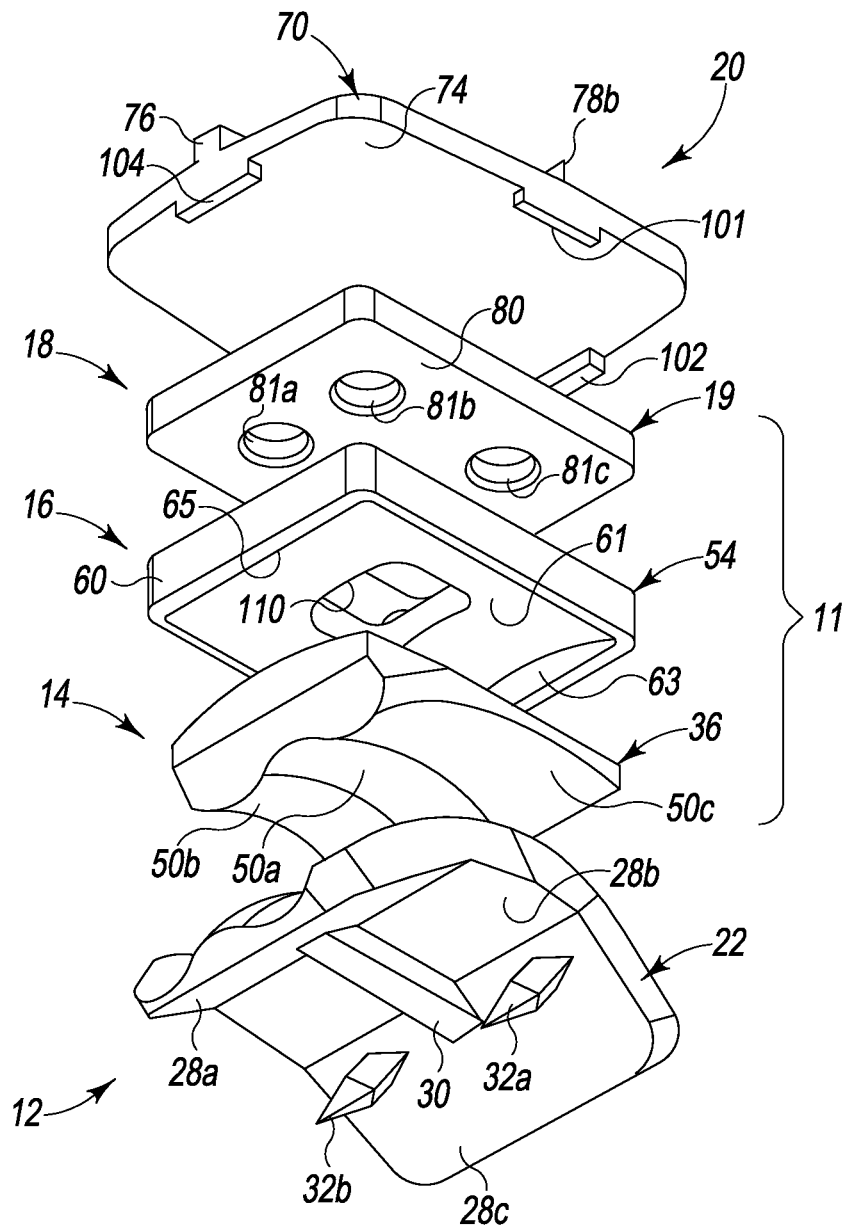
FIG. 4 is an exploded isometric inferior view of the present semi constrained right ankle joint replacement implant from a posterior/lateral viewpoint.
Figure 5:
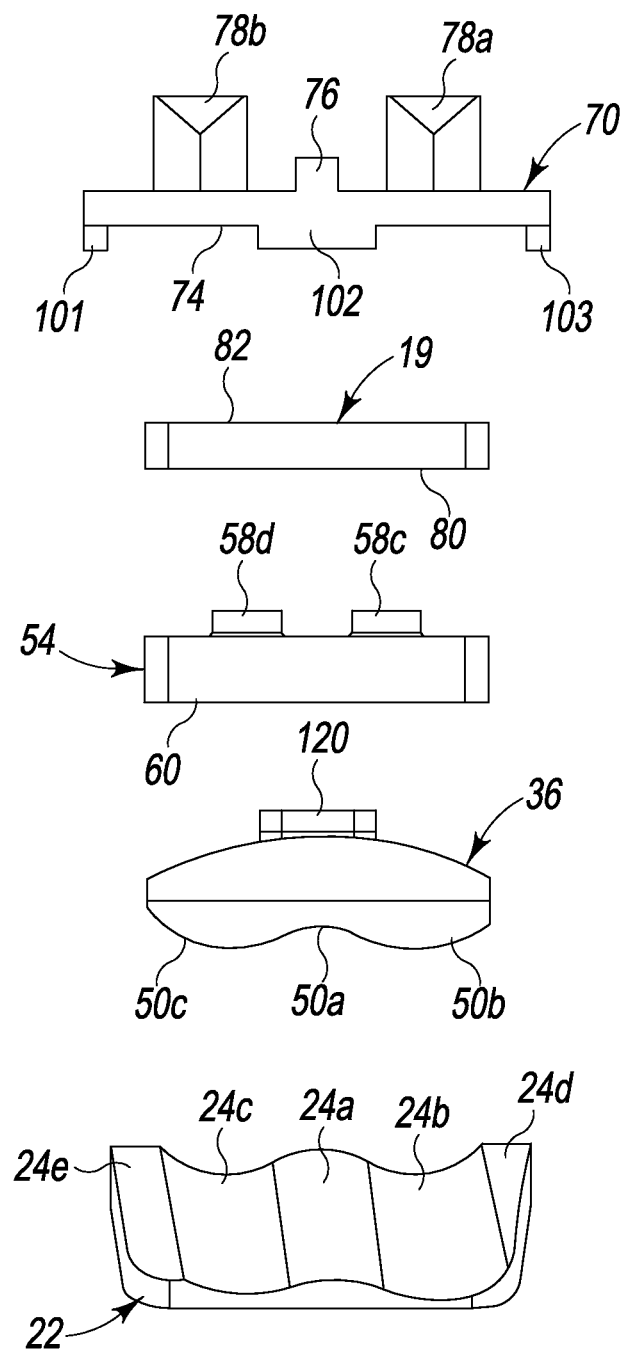
FIG. 5 is an exploded front/anterior plan view of the present semi constrained right ankle joint replacement implant.
Figure 6:
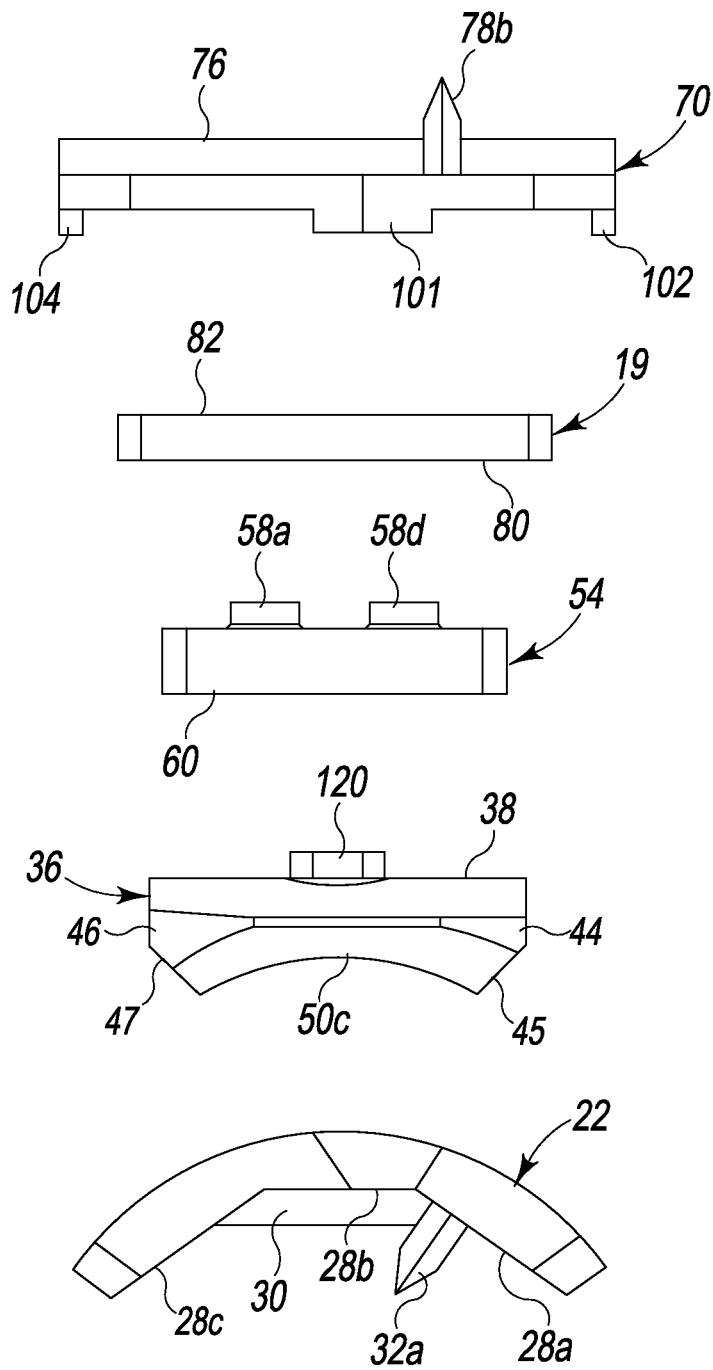
FIG. 6 is an exploded side/lateral plan view of the present semi constrained right ankle joint replacement implant.
Figure 7:
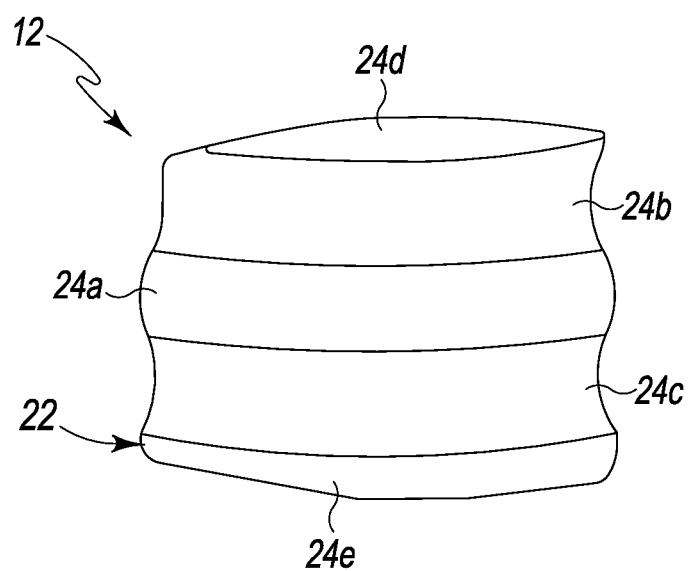
FIG. 7 is a superior plan view of the talar component of the present semi constrained right ankle joint replacement implant.
Figure 8:
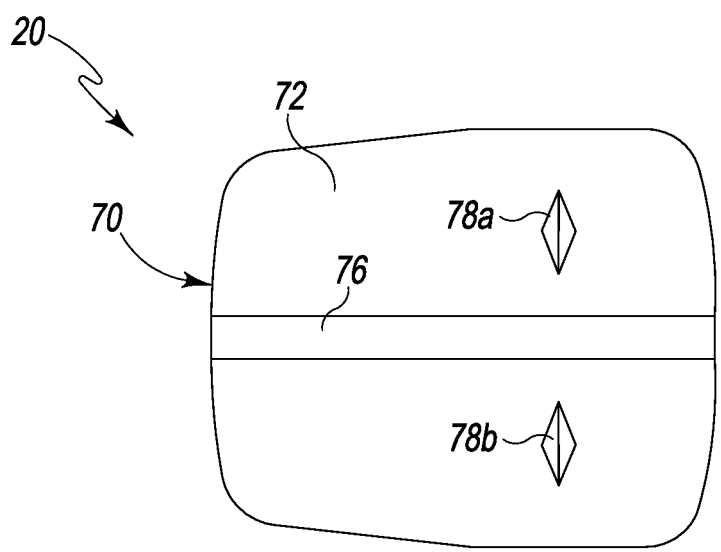
FIG. 8 is a superior plan view of the tibial component of the present semi constrained right ankle joint replacement implant.
Figure 9:
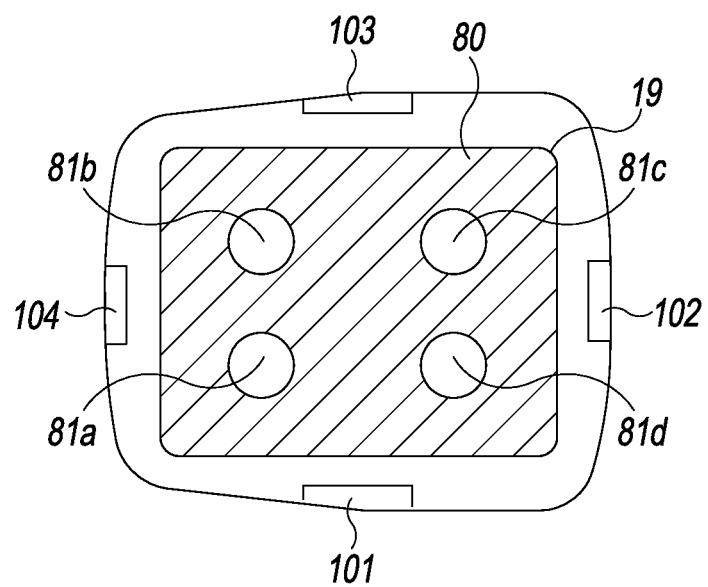
FIG. 9 is a sectional view of the present semi constrained right ankle joint replacement implant taken along line 9-9 of FIG. 13.
Figure 10:
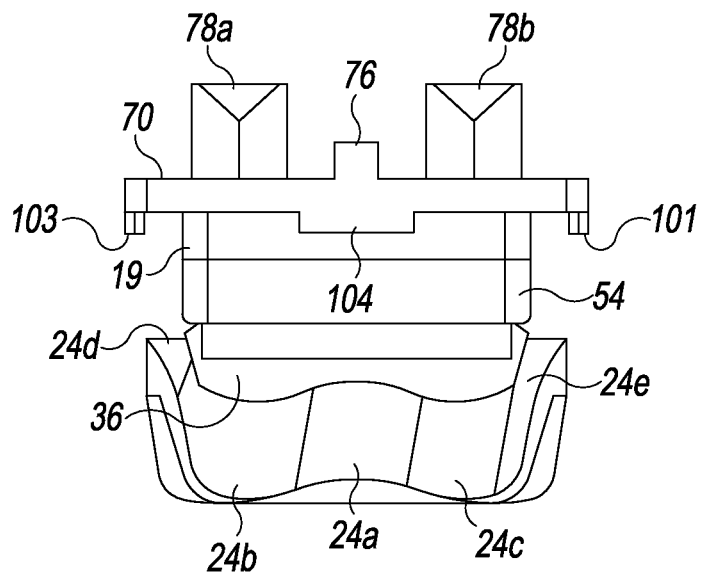
FIG. 10 is a posterior view of the present semi constrained right ankle joint replacement implant.
Figure 11:
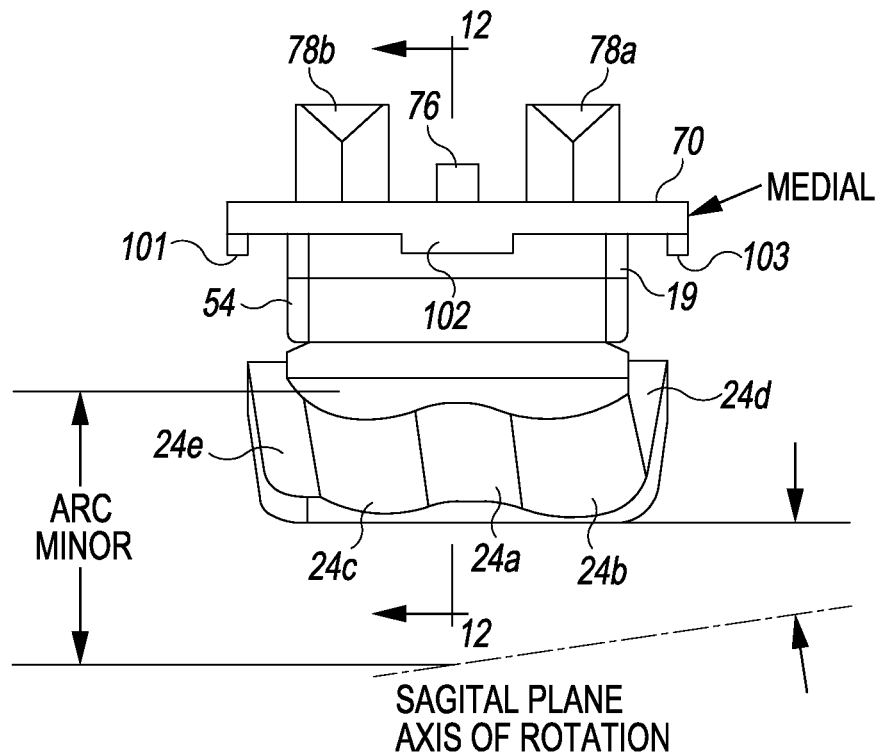
FIG. 11 is an anterior view of the present semi constrained right ankle joint replacement implant.
Figure 12:
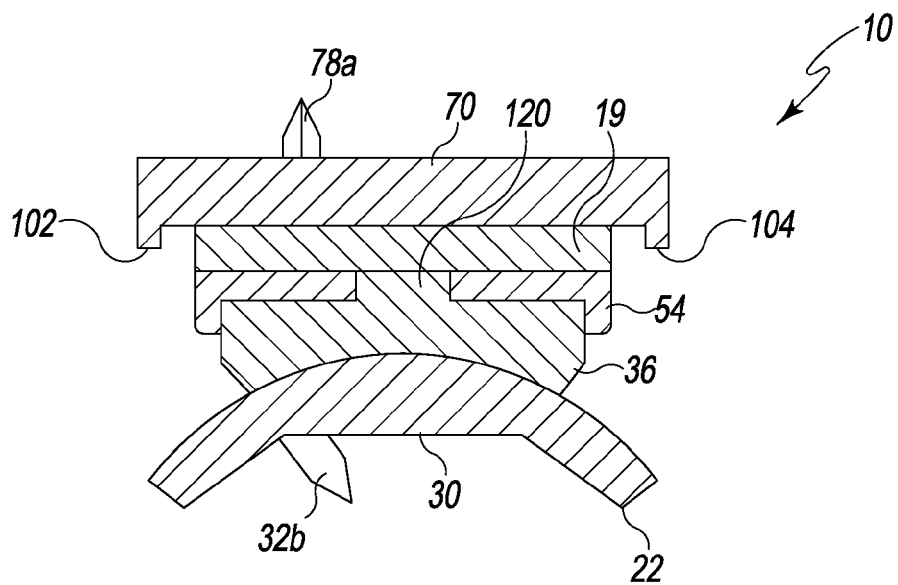
FIG. 12 is sectional view of the present semi constrained right ankle joint replacement implant taken along line 12-12 of FIG. 11.
Figure 13:
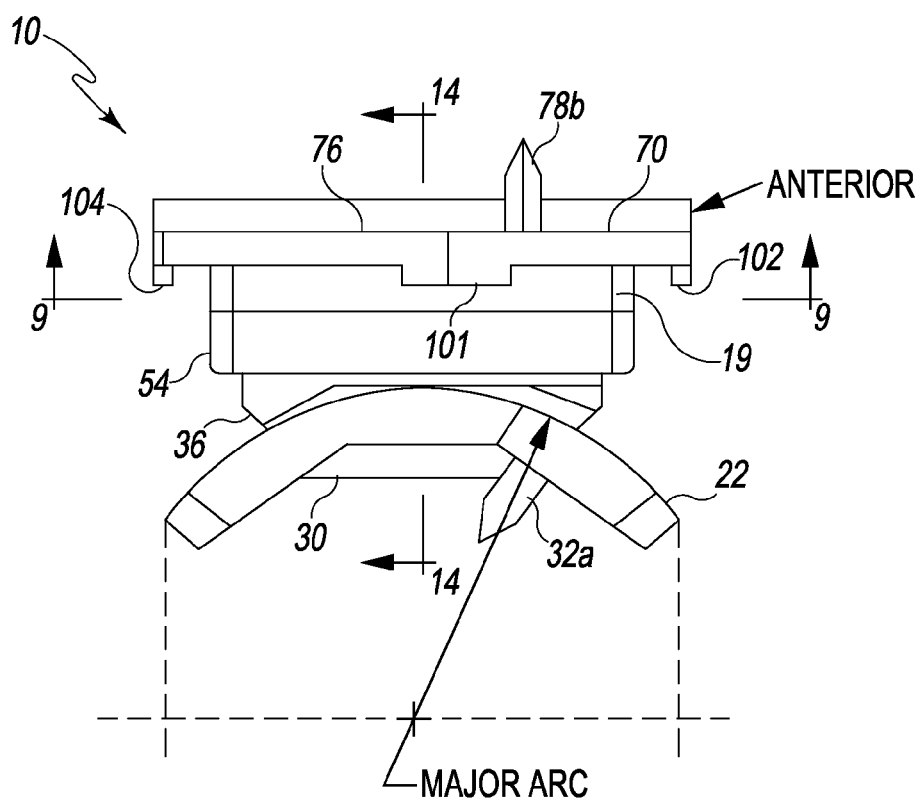
FIG. 13 is a lateral view of the present semi constrained right ankle joint replacement implant.
Figure 14:
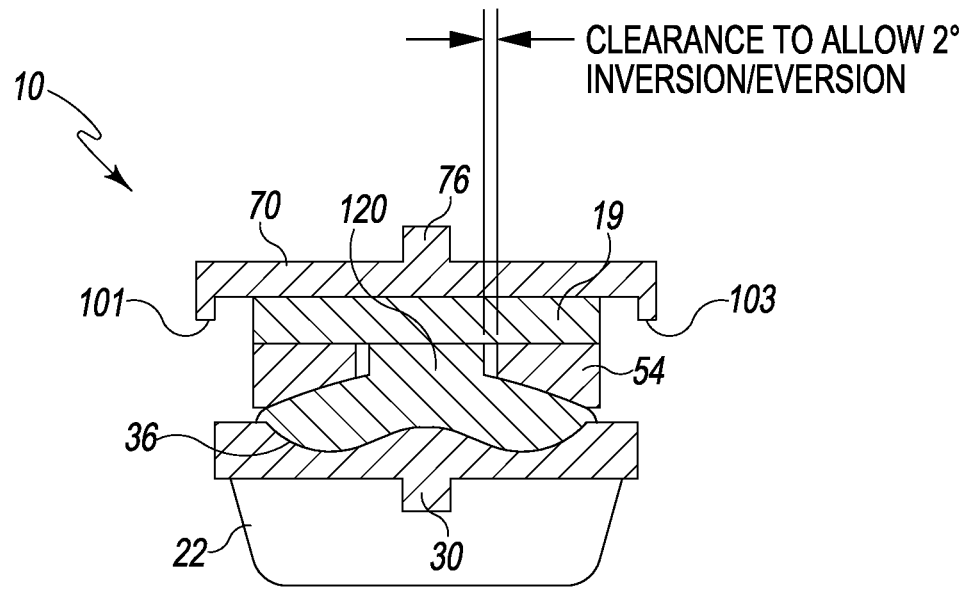
FIG. 14 is a sectional view of the present semi constrained right ankle joint replacement implant taken along line 14-14 of FIG. 13.
Figure 15:
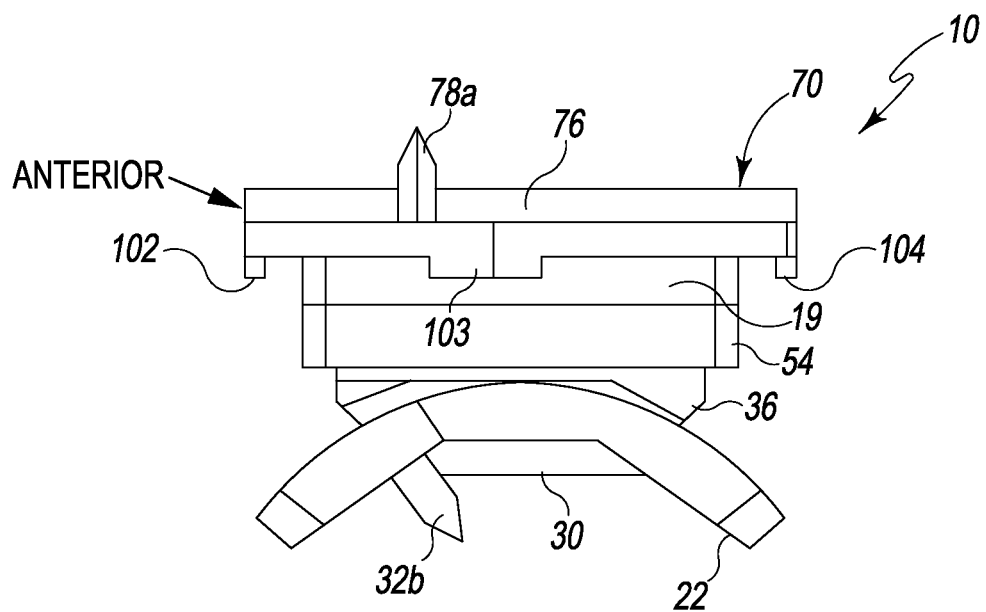
FIG. 15 is another lateral view of the present semi constrained right ankle joint replacement implant.
Figure 16:
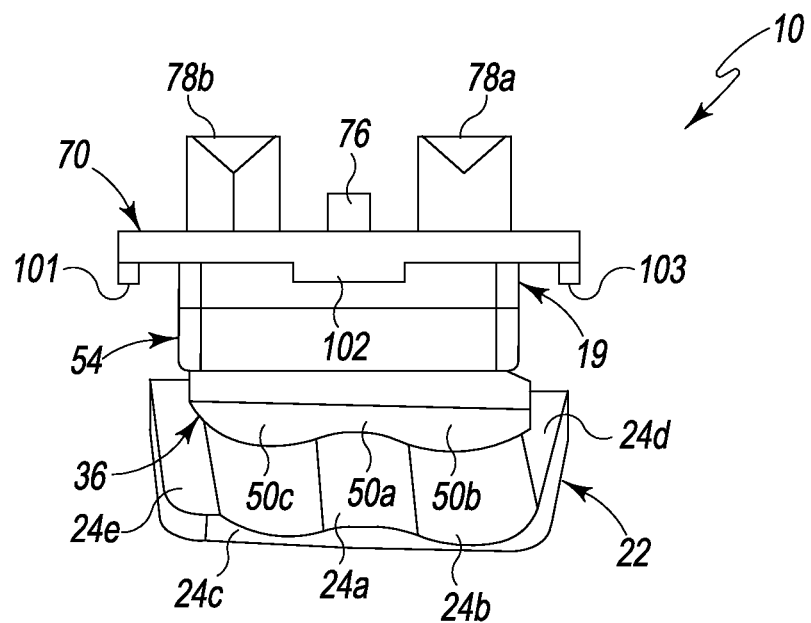
FIG. 16 is an anterior view of the present semi constrained right ankle joint replacement implant illustrating eversion translation.
Figure 17:
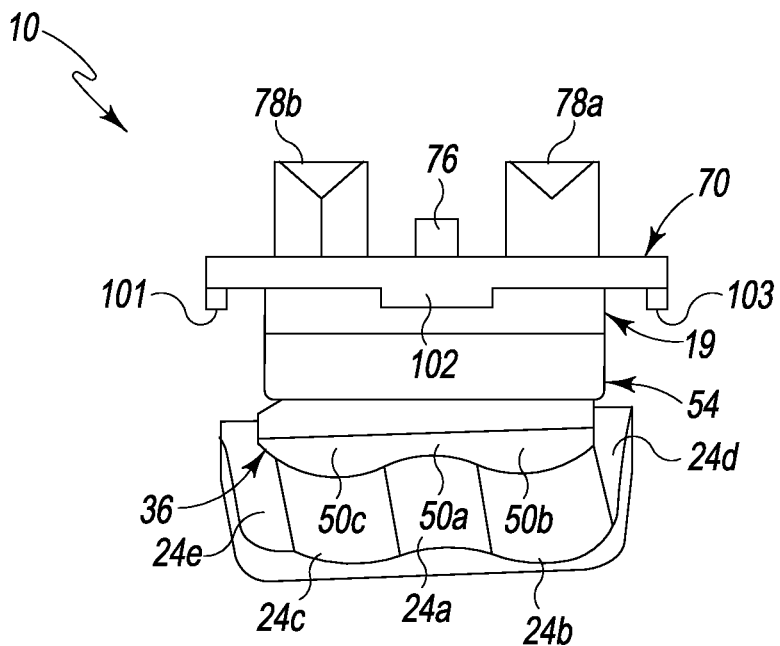
FIG. 17 is an anterior view of the present semi constrained right ankle joint replacement implant illustrating inversion translation.
Figure 18:
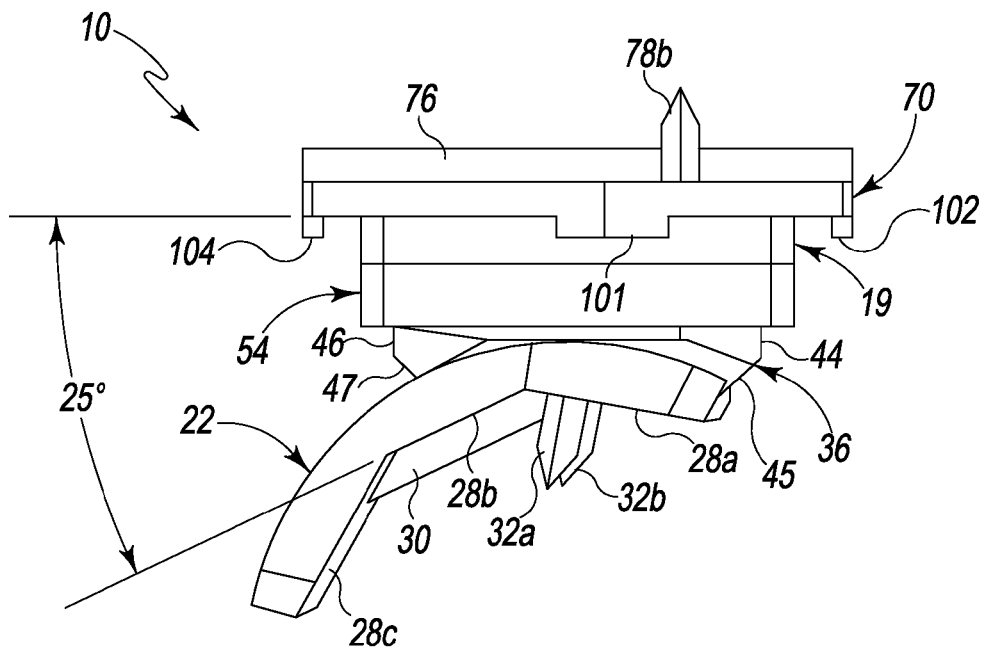
FIG. 18 is a lateral view of the present semi constrained right ankle joint replacement implant illustrating dorsiflexion translation with respect to a pivot point of the talar component.
Figure 19:
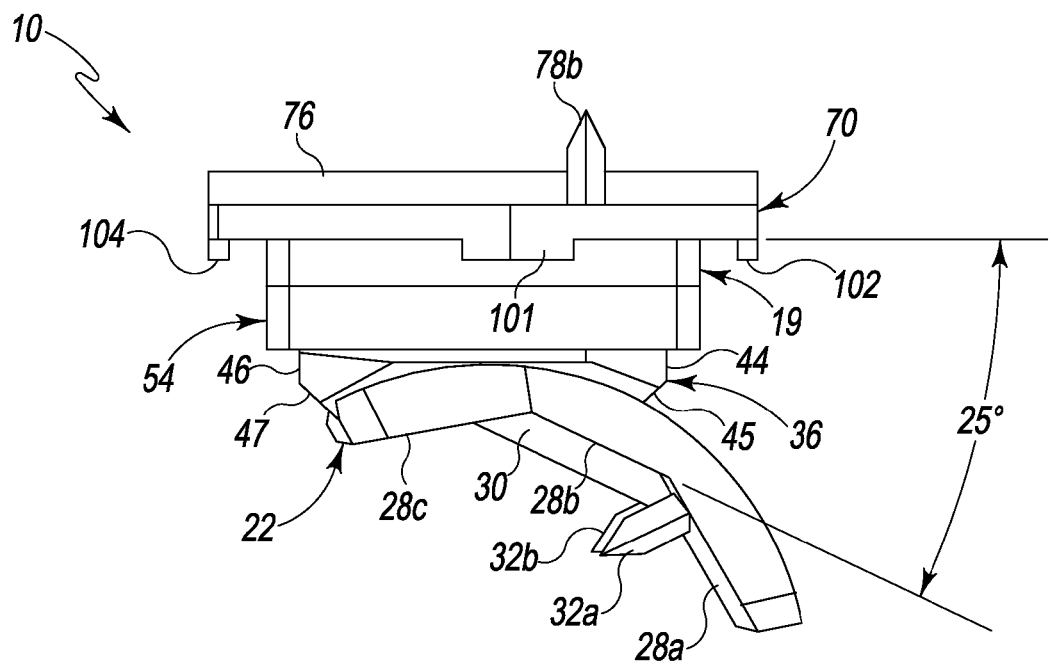
FIG. 19 is a lateral view of the present semi constrained right ankle joint replacement implant illustrating plantarflexion translation with respect to a pivot point of the talar component.

Referring to FIGS. 1-19, there is depicted a semi constrained polyaxial ankle joint replacement implant or prosthesis 10 fashioned in accordance with the present principles. The semi constrained polyaxial endoprosthetic ankle joint replacement implant 10 (i.e. ankle implant or prosthesis) has several components that interact to provide an ankle prosthesis which mimics a natural ankle joint (i.e. as between the tibia and the talus/calceneus). Particularly, the ankle prosthesis 10 includes a talus or talar (hereinafter collectively, talar) component or plate 12 that is configured for attachment to the talus or calceneus bone (not shown), a tibia or tibial (hereinafter collectively, tibial) component or plate 20 that is configured for attachment to the tibia bone (not shown), and a dual bearing component 11 situated between the talar plate 12 and the tibial plate 20 that is configured to allow articulation or translation with respect to the talar plate 12 and allow articulation or translation with respect to the tibial plate 20. In short, the dual bearing component 11 interacts with the talar plate 12 and the tibial plate 20 to provide/allow semi constrained poly-axial movement of the ankle prosthesis and thus the reconstructed ankle joint.

The tibial component 20 includes a plate 70 and other features described herein, formed of a biocompatible metal such as stainless steel, titanium, an alloy of same, or other biocompatible material. The plate 70 is generally rectangular in shape except that it narrows slightly from the anterior side of the plate 70 to the posterior side of the plate 70. The plate 70 has a generally planar and smooth superior surface 72 and a generally planar and smooth inferior surface 74. Alternatively or additionally, the superior surface 72 may be textured, porous or otherwise if desired to promote bone ingrowth and/or have a slight convex or concave contour. The superior surface 72 has a ridge or projection 76 that extends from and between the anterior side and the posterior side of the plate 70. The ridge 76 is generally rectangular in cross section along its length and serves to prevent or guard against twisting after implantation. The ridge 76 may take shapes other than rectangular. Furthermore, the ridge 76 may not extend entirely from the posterior edge of the plate 70 to the anterior edge of the plate 70. Moreover, the ridge 76 may not be continuous but instead be comprises of two or more segments. Other configurations and arrangements are contemplated.

The superior surface 72 also has a first spike, stem, point or barb (hereinafter, spike) 78a situated on one side of the ridge that extends in the superior direction and a second spike, stem, point or barb (hereinafter spike) 78b situated on another side of the ridge 76 that likewise extends in the superior direction, it being appreciated that the nomenclature first and second are arbitrary. The spikes 78a, 78b are situated proximate the anterior side of the plate 70 and are configured to extend into the tibia in order to help retain the tibial component 20 onto the tibia and prevent and/or guard against twisting after implantation. The length of the spikes 78a, 78b are subject to variation both together and separately. The spikes 78a, 78b may be optional. Preferably, but not necessarily, the tibial component 20 is machined or made from a single mass of the desired biocompatible material.

The tibial plate 70 includes a medial flange 101 that extends downwardly from the medial edge thereof, a lateral flange 103 that extends downwardly from the lateral edge thereof, a posterior flange 104 that extends downwardly from the posterior edge thereof, and an anterior flange 102 that extends downwardly from the anterior edge thereof. The peripheral tibial flanges 101, 102, 103, 104 semi constrain or limit movement between it and the superior bearing 18.

The talar component 12 includes a plate 22 formed of a biocompatible metal such as stainless steel, titanium, an alloy of same or other biocompatible material. The talar plate 22 is generally in the shape of an arc that mimics the articulation or translation arc of the natural human ankle joint. The talar plate 22 also narrows slightly from an anterior side of the talar plate 22 to the posterior side of the talar plate 22. The talar plate 22 has a smooth superior surface with several contours 24a, 24b, 24c, extending from and between the anterior and posterior sides of the talar plate 22. The superior surface has an intermediate convex contour 24a, a medial concave contour 24c and a lateral concave contour 24b. The medial side of the talar plate 22 has an arced ledge 24e while the lateral side of the talar plate 22 also has an arced ledge 24d. The arced ledges support and allows translation of a portion of the tibia thereon. The arched ledges allow a portion of an inferior bearing 14 of the dual bearing component 11 to translate thereon.

The superior surface 24 of the talar plate is angled upwardly from the medial side to the lateral side or conversely angled downwardly from the lateral side to the medial side along the anterior to posterior arcuate length of the talar plate. In a preferred form, this angle is around 7.5° however, the angle may be more or less than 7.5°. The angle mimics the natural arch of the ankle.

The inferior surface 28 of the talar plate 22 has three generally planar and smooth arcuate sections or cuts 28a, 28b, 28c that together form the plate arch. These sections or cuts correspond to the bone cuts in the prepared talar (or calceneal) bone. Alternatively or additionally, the inferior surface may be textured, porous or otherwise if desired to promote bone ingrowth. A ridge or projection 30 extends from section of the inferior surface between the sections. The ridge 30 is generally rectangular in cross section along its length and serves to prevent or guard against twisting after implantation. The ridge 30 may take shapes other than rectangular. The section 28c of the inferior surface also includes a first spike, stem, point or barb (hereinafter, spike) 32a situated on one side of the ridge 30 that extends in the inferior direction, and a second spike, stem, point or barb (hereinafter spike) 32b situated on another side of the ridge 30 that likewise extends in the inferior direction, it being appreciated that the nomenclature first and second are arbitrary. The spikes 32a, 32b are situated proximate the anterior side of the talar plate 22 and are configured to extend into the talus or calceneus bone in order to help retain the talar component 12 onto the talus or calceneus and prevent and/or guard against twisting after implantation. The length of the spikes are subject to variation both together and separately. Preferably, but not necessarily, the talar component 12 is machined or made from a single mass of the desired biocompatible material.

The dual bearing component 11 is composed of three parts; a bearing plate 16, an inferior bearing 14, and a superior bearing 18. The bearing plate 16 is defined by a plate 54 formed of a biocompatible metal such as stainless steel, titanium, an alloy of same or other biocompatible material. The plate 54 is generally in the shape of a rectangle and sized to fit under the tibial plate 70. A superior surface 58 of the plate 54 includes a plurality of projections 58a, 58b, 58c, 58d which extend in the superior direction. The projections 58a, 58b, 58c, 58d are depicted as circular tabs or cylinders but may take other shapes as desired. Moreover, while four (4) projections are shown, more or less projections may be provided. The projections 58a, 58b, 58c, 58d are preferably spaced on the superior surface 58 to provide secure connectivity to the superior bearing 18 as explained below.

The bearing plate 54 includes a rim 60 that extends about the periphery of the bearing plate 54 and projects in the inferior direction. An inferior surface 61 of the bearing plate 54 is arced or curved from a medial side thereof to a lateral side thereof within the peripheral rim 60. As such, a generally arced anterior edge 63 is formed at the anterior end of the peripheral rim 60 and a generally arced posterior edge 65 is formed at the posterior end of the peripheral rim 60. The peripheral rim 60 may have a first arced flat at the medial side and a second arced flat at the lateral side (not shown) if desired. As described below, the curved inferior surface 61, the peripheral rim 60 and the anterior and posterior ends 63, 65 provide a pocket that receives the inferior bearing 14.

The bearing plate 54 further includes a cutout 110 that is situated generally in the middle thereof. However, the cutout 110 may be positioned in other locations if desired. The cutout 110 is fashioned as a rectangle. However, other shapes may be used. Moreover, there may be more than one cutout. The multiple cutouts may be situated as desired.

The superior bearing 18 of the dual bearing component 11 is defined by a plate 19 formed of a biocompatible plastic such as polyethylene, polyetheretherketone (PEEK), polytetrafluoroethylene (PTFE), another biocompatible plastic, or other biocompatible material that provides a gliding bearing surface. The superior bearing plate 19 is generally in the shape of a rectangle and sized to fit onto the superior surface 58 of the bearing plate 54. The superior bearing plate 19 has a generally planar and smooth superior surface 82 and a generally planar and smooth inferior surface 80. The inferior surface 80 has a plurality of indentations 81a, 81b, 81c, 81d which extend in the inferior direction. The indentations 81a, 81b, 81c, 81d are depicted as circular bores or concavities to coincide with the shape of the projections of the bearing component, but may take other shapes as desired as long as they coincide and/or cooperate with the projections 58a, 58b, 58c, 58d of the bearing component 16. Moreover, while four (4) indentations are shown, more or less indentations may be provided, again as long as they coincide and/or cooperate with the projections of the bearing component. The indentations 81a, 81b, 81c, 81d are thus preferably spaced on the inferior surface 80 to coincide with the spacing of the projections 58a, 58b, 58c, 58d of the bearing component 16 to provide secure connectivity to the bearing component 16. The superior bearing 18 is bonded to the bearing plate 54.

The inferior bearing 14 of the dual bearing component 16 is defined by an inferior bearing plate 36 formed of a biocompatible plastic such as polyethylene, polyetheretherketone (PEEK), polytetrafluoroethylene (PTFE), another biocompatible plastic, or other biocompatible material that provides a gliding bearing surface. The inferior bearing plate 36 is generally in the shape of a rectangle but narrows slightly from the anterior side 44 thereof to the posterior side 46 thereof the plate 36. A superior side 38 of the inferior bearing plate 36 is smooth and arced from a lateral side 41 to a medial side 42 thereof. The arc of the superior side 38 corresponds to the arc of the inferior side 61 of the bearing plate 54.

The anterior side 44 of the inferior bearing plate 36 is generally arc shaped and corresponds to the arced anterior inside edge of the bearing plate 54. Likewise, the posterior side 46 of the inferior bearing plate 36 is generally arc shaped and corresponds to the arced posterior inside edge of the bearing plate 54. Moreover, the anterior side 44 has a lower angle 45 that angles inwardly towards the inferior surface. Likewise, the posterior side 46 has a lower angle 47 that angles inwardly towards the inferior surface.

The curved and contoured superior surface 24 of the talar component 12 thus includes first and second sagital longitudinal concave grooves extending from the anterior side to the posterior side and a first sagital longitudinal convex ridge situated between the first and second sagital longitudinal concave grooves. A radius of the first and second sagital longitudinal concave grooves and of the first sagital longitudinal convex ridge vary with a minor arc existing laterally and becoming greater medially for anatomic-like tracking of the talar component 12 relative to the inferior bearing 14.

The upper part of the inferior bearing plate is thus sized to fit into the pocket or area formed by the curved inferior surface, the peripheral rim and the anterior and posterior ends of the bearing plate. The inferior bearing plate 36, however, is not bonded to the bearing plate 18 but is relatively free to translate in the medial/lateral directions relative to the bearing plate. The lip may be considered a tracking lip that extends inferiorly around the periphery of the bearing located in both the anterior and posterior aspects. The tracking lip of the bearing component plate that catches, guides and prevents the inferior bearing from dislodging from the bearing component plate in the anterior and posterior directions.

The inferior surface is generally smooth with several contours 50a, 50b, 50c extending from and between the lower angle 45 of the anterior side 44 and the lower angle 47 of the posterior side 46 of the plate 36. The inferior surface has an intermediate concave contour 50a, a medial convex contour 50c, and a lateral convex contour 50b. The contours correspond oppositely to the contours of the superior surface of the talar plate 22. Particularly, the contours of the inferior bearing 14 fit into the contours of the talar component 12. This allows translation or articulation between the talar component 12 and the inferior bearing 14.

The superior surface 38 of the inferior bearing 14 has a flange 120 extending therefrom and transverse thereto. The flange 120 is configured for reception in the cutout 110 of the intermediate (bearing) plate 54 to semi constrain and/or limit movement relative between the two components. The flange 120 is situated on the superior surface 38 to coincide with the placement of the cutout 110. If there are more than one cutouts, there will be more than one flange (i.e. a one-to-one correspondence).

The dual bearing component 11 thus provides a superior bearing surface for the tibial component 20 that allows semi constrained articulation/translation of the dual bearing component 11 relative to the tibial component 20 in order to provide/allow eversion and inversion. The dual bearing component 11 and the talar component 12 provide up to 7° (preferably 2°) of eversion relative to the tibial component 20. The tibial component 20 also slides about the superior bearing 18. This allows sideways movement of the foot.

The dual bearing component 11 thus provides an inferior bearing surface for the talar component 12 that allows articulation/translation of the talar component 12 relative to the dual bearing component 11 in order to provide/allow dorsiflexion and plantarflexion. The talar component 12 provides up to 25° dorsiflexion relative to the pivot point (vertical centerline of the tibial component) for the talar plate (see e.g., FIGS. 18 and 19). This allows up/down movement of the foot.

While not shown, in a variation, the anterior to posterior fin of the talar plate may be slightly longer from posterior to anterior as shown in the figures and include two holes to accept two laterally placed locking screws. The two holes for the locking screws may be provided in two lateral flanges extending anterior to posterior in the inferior surface of the tibial component. Additionally, the anchoring stems or spikes of the talar plate may be located in the anterior 1/3 of the inferior surface and slightly angled from superior/anterior to inferior/posterior.

While not shown, in another variation, the tibial component may have a lateral and dorsal flange to accept two locking fixation screws from lateral to medial across the superior surface of the tibial plate.

It should be appreciated that although the present ankle joint replacement implant, systems and methods set forth herein are described in detail in connection with the ankle joint, the implant and/or principles of the present invention also has application for use with other joints throughout the body, such as for example, both the spine and wrist, with an upper or proximal fixation portion, a dual bearing design, and a lower or distal fixation component.

Moreover, while the invention has been illustrated and described in detail in the drawings and foregoing description, the same is to be considered as illustrative and not restrictive in character, and that all changes and modifications that come within the spirit of the invention are desired to be protected.

What is claimed is:

1. A semi constrained polyaxial ankle implant comprising:
   a first bone anchoring component having an inferior surface;
   a second bone anchoring component having a superior surface; and
   a dual bearing component positioned between the first bone anchoring component and the second bone anchoring component, the dual bearing component having a superior bearing with a superior surface in contact with the inferior surface of the first bone anchoring component and allowing motion between the first bone anchoring component and the superior bearing, an inferior bearing with an inferior surface in contact with the superior surface of the second bone anchoring component and allowing motion between the second bone anchoring component and the inferior bearing, and a plate positioned between the superior bearing and the inferior bearing, the plate having a superior surface, an inferior surface, and an opening extending from the inferior surface to the superior surface;
   the first bone anchoring component having peripheral, transversely extending flanges that extend over sides of the superior bearing and which limits motion between the first bone anchoring component and the superior bearing;
   the inferior bearing having a superior surface, and a flange extending upwardly from the superior surface, the flange received in the opening in the plate whereby motion is partially limited between the inferior bearing and the plate.

2. The semi constrained polyaxial ankle implant of claim 1, wherein the superior bearing of the dual bearing component is bonded to the plate of the dual bearing component.

3. The semi constrained polyaxial ankle implant of claim 2, wherein the superior bearing has an inferior surface with a plurality of cavities, the plate has a plurality of projections on the superior surface that correspond in number to the plurality of cavities, and the projections are received in the cavities.

4. The semi constrained polyaxial ankle implant of claim 3, wherein:
   the first bone anchoring component is configured to attach to a tibia; and
   the second bone anchoring component is configured to attach to a talus.

5. The semi constrained polyaxial ankle implant of claim 4, wherein the second bone anchoring component has an inferior surface with a bone fixation portion for fixation to the talus, and the superior surface is configured complementarily congruent with the inferior surface of the inferior bearing of the dual bearing component.

6. The semi constrained polyaxial ankle implant of claim 5, wherein the first bone anchoring component has a superior surface with a bone fixation portion for fixation to the tibia, and the inferior surface is complementarily congruent with the superior surface of the superior bearing of the dual bearing component.

7. The semi constrained polyaxial ankle implant of claim 5, wherein the inferior bearing has a contoured inferior surface that is congruent with a complementarily contoured superior surface of the second bone anchoring component that allows frontal plane motion but limits transverse and sagittal plane motion.

8. A polyaxial ankle implant comprising:
   a tibia anchoring component having an inferior surface;
   a talar anchoring component having a superior surface; and
   a dual bearing component positioned between the tibia anchoring component and the talar anchoring component, the dual bearing component having a superior bearing with a superior surface in contact with the inferior surface of the tibia anchoring component and allowing motion between the tibia anchoring component and the superior bearing, an inferior bearing with an inferior surface in contact with the superior surface of the talar anchoring component and allowing motion between the talar anchoring component and the inferior bearing, and a plate positioned between the superior bearing and the inferior bearing, the plate having a superior surface, an inferior surface, and an opening at a middle thereof extending from the inferior surface to the superior surface;
   the tibia anchoring component having a peripheral, transversely extending flange on each side thereof that extends over each side of the superior bearing that limits motion between the tibia anchoring component and the superior bearing;
   the inferior bearing having a superior surface, and a flange extending upwardly from the superior surface, the flange received in the opening in the plate whereby motion is partially limited between the inferior bearing and the plate.

9. The polyaxial ankle implant of claim 8, wherein the superior bearing of the dual bearing component is bonded to the plate of the dual bearing component.

10. The polyaxial ankle implant of claim 9, wherein the superior bearing has an inferior surface with a plurality of cavities, the plate has a plurality of projections on the superior surface that correspond in number to the plurality of cavities, and the projections are received in the cavities.

11. The polyaxial ankle implant of claim 10, wherein the talar anchoring component has an inferior surface with a bone fixation portion for fixation to the talus, and the superior surface is configured complementarily congruent with the inferior surface of the inferior bearing of the dual bearing component.

12. The polyaxial ankle implant of claim 11, wherein the tibia anchoring component has a superior surface with a bone fixation portion for fixation to the tibia, and the inferior surface is complementarily congruent with the superior surface of the superior bearing of the dual bearing component.

13. The polyaxial ankle implant of claim 11, wherein the inferior bearing has a contoured inferior surface that is congruent with a complementarily contoured superior surface of the talar anchoring component that allows frontal plane motion but limits transverse and sagittal plane motion.

* * * * *